United States Patent [19]

Kimura et al.

[11] Patent Number: 4,893,503
[45] Date of Patent: Jan. 16, 1990

[54] METHOD OF MEASURING ADHESIVE STRENGTH OF ADHESIVE SHEET AND APPARATUS FOR IMPLEMENTING THIS METHOD

[75] Inventors: Akira Kimura, Suita; Osamu Tomita, Osaka, both of Japan

[73] Assignee: Kanzaki Paper Manufacturing Co., Tokyo, Japan

[21] Appl. No.: 208,417
[22] PCT Filed: Apr. 30, 1987
[86] PCT No.: PCT/JP87/00274
§ 371 Date: May 17, 1988
§ 102(e) Date: May 17, 1988
[87] PCT Pub. No.: WO88/02484
PCT Pub. Date: Apr. 7, 1988

[30] Foreign Application Priority Data

Sep. 27, 1986 [JP] Japan .................. 61-2288040

[51] Int. Cl.⁴ .................................. G01N 19/04
[52] U.S. Cl. ........................ 73/150 A; 73/827; 73/829
[58] Field of Search ............. 73/150 R, 150 A, 827, 73/829, 834, 842

[56] References Cited

U.S. PATENT DOCUMENTS

| 2,834,205 | 5/1958 | Pickup | 73/827 |
| 3,019,644 | 2/1962 | Mancini | 73/827 |
| 3,394,588 | 7/1968 | Mohle et al. | 73/150 A |
| 3,412,606 | 11/1968 | Cooper et al. | 73/150 A |
| 3,524,345 | 8/1970 | Isaacson | 73/150 A |
| 4,294,111 | 10/1981 | Rutledge et al. | 73/150 R |

FOREIGN PATENT DOCUMENTS

| 1948897 | 4/1971 | Fed. Rep. of Germany | 73/150 A |
| 15192 | 2/1978 | Japan . | |
| 62887 | 5/1979 | Japan . | |
| 57-44834 | 3/1982 | Japan | 73/150 A |
| 62-261029 | 11/1987 | Japan | 73/150 A |
| 139129 | 12/1961 | U.S.S.R. | 73/150 A |
| 389444 | 7/1973 | U.S.S.R. | 73/150 A |
| 551126 | 2/1943 | United Kingdom | 73/150 A |
| 610232 | 10/1948 | United Kingdom | 73/150 A |
| 1536864 | 12/1978 | United Kingdom | 73/827 |

OTHER PUBLICATIONS

"Peel Resistance Accurately Measured", Materials Research & Standard (NASA Tech Brief B65–10173), p. 435 (Aug. 1965).
Schweiger, R. L., "How a Release and Adhesion Tester was Developed for Pressure-Sensitive Labels", Adhesives Age, vol. 13, No. 5, pp. 34–36, (May 1970).
Herrman, R. C. and Dunn H. F., "Determining the Peel Strength of Adhesive Bonds Between Flexible Materials, Materials Research and Standards," vol. 10, No. 12 p. 27 (Dec. 1970).

Primary Examiner—William A. Cuchlinski, Jr.
Assistant Examiner—Diego F. F. Gutierrez
Attorney, Agent, or Firm—Morgan & Finnegan

[57] ABSTRACT

A method of measuring adhesive strength is disclosed, characterized by the steps of:
keeping the surface of a substrate adhered with an adhesive sheet in a fixed relative position to the pickup roller an auxiliary roller projecting from a machine frame;
securing the tip end of either the adhesive sheet or the lead-in tape leading said adhesive sheet to the pickup roller;
setting a specific peeling angle for peeling the adhesive sheet from the surface of the substrate;
pulling the adhesive sheet by rotating the pickup roller at a constant speed while maintaining the set angle;
peeling off the adhesive sheet 2 from the substrate, and subsequently winding it onto the pickup roller;
detecting the torque of the pickup roller using a torque detector; and
displaying and/or recording the adhesive strength of the adhesive sheet to said substrate based on output signals from the torque detector.

5 Claims, 5 Drawing Sheets

METHOD OF MEASURING ADHESIVE STRENGTH OF ADHESIVE SHEET AND APPARATUS FOR IMPLEMENTING THIS METHOD

TECHNICAL FIELD

The present invention relates to a method and an apparatus for easily measuring the adhesive-strength of an adhesive sheet to the adhered substrate, and more particularly to a compact and portable apparatus which is capable of quickly and easily measuring adhesive-strength.

BACKGROUND ART

Conventionally, a variety of tests are carried out against adhesive sheets for checking adhesive-strength, retention strength, tacking strength, or the like. Adhesive characteristic being one of such test items is represented by adhesive strength which is measured at the time of peeling off the adhesive sheet from a specific substrate at 180° or 90° of angle against the surface of the substrate adhered with the peeled portion of the adhesive sheet. For example, adhesive-strength at the time of peeling off the adhesive sheet from the adhered substrate at right angles denotes the strength of inhibiting the adhesive sheet from being peeled off from the surface of the adhered substrate in the vertical direction.

Based on JIS (Japan Industrial Standard), the adhesive-strength is calculated from load which is applied at the time of peeling off the adhesive sheet from the adhered substrate at a constant speed. However, since any of those conventional adhesive-strength measuring apparatuses securely fixes the substrate itself adhered with adhesive sheet onto the surface of the apparatus to hold the tip end of the adhesive sheet to be peeled off from the adhered substrate, the adhesive-strength measuring apparatus is provided with large dimensions and weight to result in the inconvenience for carrying it to a specific location.

Concretely, when measuring the adhesive strength at the time of peeling off the adhesive sheet from the substrate at right angles, since the peeling position shifts as the peeling operation goes on, either the substrate fixed part, or the mechanism of the apparatus which pulls the adhesive sheet from the substrate should precisely and delicately be moved to prevent the peeling angle from varying. However, in order to correctly move them in accordance with the predetermined peeling speed, any of these conventional measuring apparatuses is compulsorily provided with a complex and large constitution.

This in turn causes much inconvenience to an operator to carry the large and heavy measuring apparatus to and from the designated location. In addition, since the operator needs to carry the substrate adhered with adhesive sheet to the apparatus-installed position for setting it to the apparatus, the operator cannot immediately measure the adhesive-strength of the adhesive sheet adhered to an optional substrate as required.

DISCLOSURE OF INVENTION

The primary object of the invention is to overcome the above-mentioned problem by providing a compact and portable apparatus which is capable of adhering an adhesive sheet to a preselected substrate and then quickly measuring the adhesive-strength on the spot.

Another object of the invention is to provide a novel apparatus which is applicable to either 90° peeling or 180° -peeling operation and capable of maintaining the peeling speed and angle constant independent of the flatness and curvature of the surface of the substrate adhered with adhesive sheet so that the apparatus itself can precisely measure the adhesive-strength.

The invention provides a method of measuring the adhesive-strength of adhesive sheets comprising the steps of:

keeping the surface of a substrate adhered with an adhesive sheet except for at least its tip portion in a fixed relative position against the pickup roller by means of an auxiliary roller;

securing the free end portion of either the adhesive sheet or a lead-in tape leading the adhesive sheet to engaging means provided on the above pickup roller;

setting the adhesive-sheet peeling angle against the surface of the substrate to the predetermined angle;

peeling off the adhesive sheet from the substrate and winding it onto the pickup roller by rotating the pickup roller at a constant speed while maintaining the setup angle;

detecting the torque of the pickup roller by applying a torque detector; and displaying and/or recording adhesive strength of the adhesive sheet to the substrate in accordance with signal output from the torque detector.

On the other hand, the adhesive-strength measuring apparatus related to the invention is provided with the following constituents:

a pickup roller having means for fixing either the tip end of the adhesive sheet or an end of the lead-in tape leading the adhesive sheet by adhesion to the tip end of the adhesive sheet;

an auxiliary roller for keeping the relative position constant between the pickup roller and the surface of the substrate adhered with the adhesive sheet except for its tip portion;

drive means for driving the pickup roller at a constant rotation speed;

torque detecting means for generating output signals by detecting the rotation force of the pickup roller; and display means for displaying the adhesive strength of the adhesive sheet to the substrate in accordance with signals output from the torque detector.

BRIEF DESCRIPTION OF DRAWINGS

FIG. 10 A through C are illustrations of another embodiment of head-chips related to the invention;

BEST MODE FOR CARRYING OUT THE INVENTION

Referring now more particularly to FIGS. 1 through 7, details of the method of measuring adhesive-strength and the related measuring apparatus embodied of the invention are described below. It should be understood, however, that the spirit and scope of the invention are not confined themselves to the following preferred embodiments.

Figure 1:
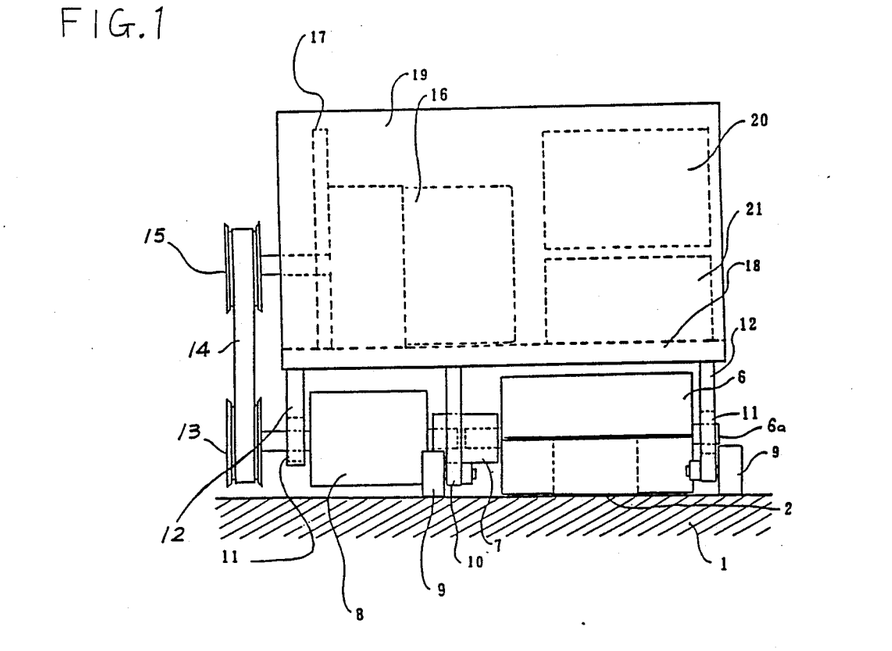
FIG. 1 is the simplified front view of a preferred embodiment of the adhesive-strength measuring apparatus according to the invention.

FIG. 1 is the simplified front view of one of the preferred embodiments of the adhesive-strength measuring apparatus according to the invention. In FIG. 1, the reference numeral 18 denotes the base plate. Bracket 12 supporting bearing 11 is provided below the base plate 18, while the bracket 12 also supports the rotary shaft $6a$ of the pickup roller 6. Torque detector is installed to an end of the rotary shaft of the pickup roller 6 via coupling 7.

Motor 16, provided with reduction gear for rotating the pickup roller 6, is secured to the upper position of the base plate 18 together with the motor-supporting frame. The rotation of the motor 16 is transmitted to the pickup roller 6 through timing pulley 15 on the part of motor 16, timing belt 14, and timing pulley 13 on the part of the pickup roller 6, thus allowing the pickup roller 6 to rotate at a constant speed.

Output signal detected by the torque detector 8 is delivered to amplifier and A/D converter (both are not shown in FIG. 1), and then the amplified and digitalized signal is displayed on the digital display 20 every moment as the adhesive-strength value. It is also possible for the system to record analog output signal on the chart using recorder 21.

As is clear from FIGS. 1 and 2, each unit of auxiliary rollers 9 is installed to the front, rear, left and right positions below the pickup roller 6. Since these auxiliary rollers respectively move in the horizontal direction while properly maintaining the vertical-position relationship between the surfaces of the pickup roller 6 and the substrate 1, these rollers 9 can rotate in contact with the surface of the substrate 1. Bearing of the auxiliary roller 9 shown to the right of FIG. 1 is secured to the lengthy opening hole or slot in the lower part (shown in FIG. 2) of bracket 12 supporting the bearing of the pickup roller 6 in the center position with screws, thus allowing the vertical position to be freely adjusted. The auxiliary roller bracket 10 is provided with a constitution identical to that of bracket 12 for adjusting the position of the auxiliary roller 9 shown to the left of FIG. 1. It is desirable that each auxiliary roller 9 be positioned to the outside of the widthwise direction (the left and right directions) of the pickup roller 6 so that each auxiliary roller 9 will not pass the upper position of the adhesive sheet to be measured in the front and rear positions of the pickup roller 6.

Figure 2:
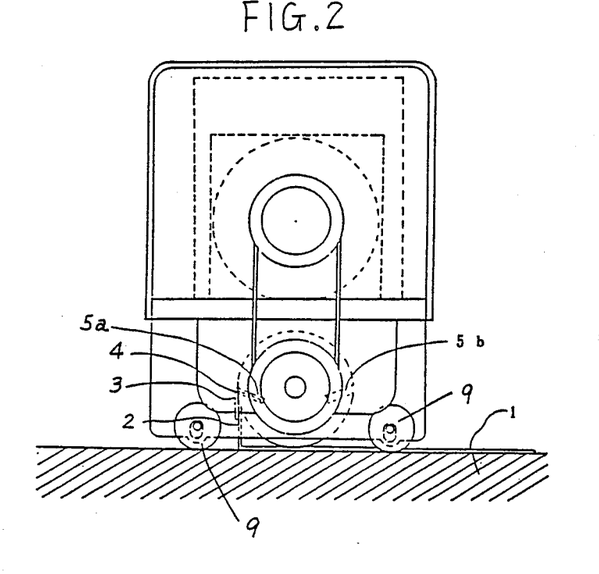
FIG. 2 is the simplified lateral view of the adhesive-strength measuring apparatus shown in FIG. 1.
Figure 3:
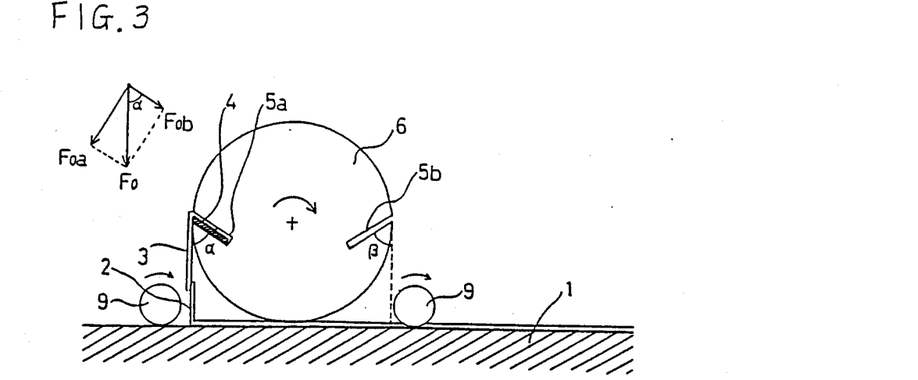
FIG. 3 is the schematic diagram illustrating the state when starting with the adhesive-strength measuring operation by implementing 90° -peeling with the apparatus shown in FIGS. 1 and 2.
Figure 4:
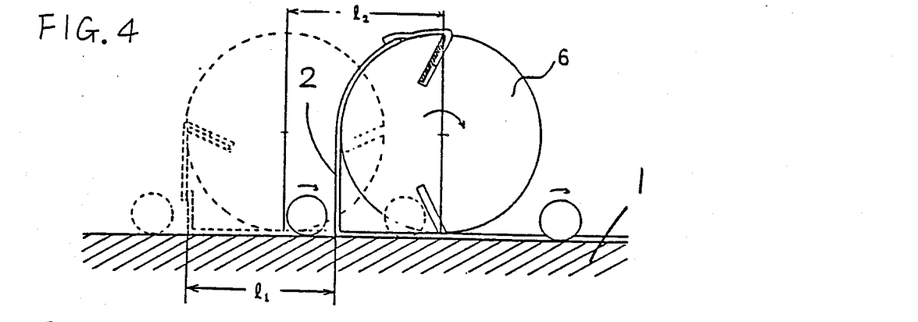
FIG. 4 is the schematic diagram illustrating the state when the adhesive sheet was peeled off from the substrate by a length l 1 from the original position of FIG. 3.

Referring now to FIGS. 2 through 4, the method of measuring the adhesive-strength via 90°-peeling mode is described below.

FIG. 2 is the simplified lateral view of a preferred embodiment of the adhesive-strength measuring apparatus related to the invention. FIG. 3 is the schematic diagram illustrating the state when starting with the measurement of the adhesive-strength via 90°-stripping mode. Pickup roller 6 is provided with a pair of engaging groove $5a$ and $5b$ which are symmetrically disposed and selectively used in accordance with the angle of stripping the adhesive sheet. More particularly, the engaging groove $5a$ is used for peeling the adhesive sheet at 90°-mode, whereas the engaging groove $5b$ is used for peeling the adhesive sheet at 180° mode. Angles $\alpha$ and $\beta$ shown in FIG. 3 are respectively the acute angles of less than 90°, which are formed between the depthwise directions of the engaging grooves $5a$ and $5b$ and the lower circumferential tangents of the pickup roller 6.

Except for the tip portion, the main portion of the adhesive sheet 2 adheres itself to the surface of the substrate 1. If the tip portion being in the initial state shown in FIG. 2 is of the length that does not reach the engaging groove $5a$ of the pickup roller 6, it is possible for the system to substantially connect the tip end of the adhesive sheet 2 to the pickup roller 6 by first allowing the rear end of a lead-in tape 3 made freom either plastic material or paper having the same width as that of the adhesive sheet 2 to be adhered to the edge portion of the adhesive sheet 2 and then inserting the header unit composed of the tip end of the lead-in tape 3 and the head chip 4 into the engaging groove $5a$ by allowing the tip end of the lead-in tape 3 to be bonded with rectangular and substantially rigid head chip 4 at the position behind the rotating pickup roller 6.

If the adhesive sheet 2 has a sufficient length, the tip end of the adhesive sheet 2 may directly be adhered to the head chip 4 by dispensing with the lead-in tape 3. When this operation is underway, a loop should be formed by adhering the adhesive surface of the tip end of the adhesive sheet 2 winding the head chip 4 by one round to the adhesive surface of the adhesive sheet 2 which is positioned immediately in front of the head chip 4 so that the tip end of the adhesive sheet 2 will not be stripped off from the head chip 4 by force of tension.

At the time of starting with the adhesive-strength measuring operation, if the head chip 4 is substantially rigid with its edge outside of the engaging slot remains without being peeled off from the free edge closest to the engaging slot of the adhesive sheet 2 or the lead-in tape 3, and yet, if the thickness of the header unit including the thickness of either the adhesive sheet 2 or the lead-in tape 3 is slightly narrower than the width of the engaging groove 5, as far as the sheet-side edge of the head chip 4 substantially projects from the inlet of the groove $5a$, the adhesive strength Fo which is present at the time of peeling off the adhesive sheet 4 from the substrate functions itself by being divided into two forces, i.e., force Foa that presses the head chip 4 against the inner surface (behind the rotation of the pickup roller) of groove 5a and force Fob that presses the head chip 4 inwardly. Consequently, the tip portion of the adhesive sheet 2 or the lead-in tape 3 can properly be held inside of slot 5a by inserting the head chip 4 attached to the tip portion of either the adhesive sheet 2 or the leading tape 3 into groove 5a, thus eventually allowing the adhesive-strength measuring apparatus to correctly measure the adhesive strength (delivery of tension to either the adhesive sheet or the leading tape).

When adhering the tip end of either the adhesive sheet 2 or the lead-in tape 3 to the head chip 4, in order to generate the divided force Fob, it is desirable for the system to correctly position the tip end of the adhesive sheet 2 or the lead-in tape 3 in the front side of the rotation of the pickup roller 6 when inserting these adhered objects into the engaging slot. However, when dealing with the adhesive sheet 2, in order to effectively use the adhesive surface, the tip end of the adhesive sheet 2 is set to the position behind the rotation of the pickup roller 6 when 90° -peeling mode is underway. When dealing with the lead-in tape 3, after adhering its tip end to the head chip 4, the lead-in tape is wound onto the head chip by one round. This allows the lead-in tape 3 to be firmly fixed inside of the engaging groove 5a without causing deviation and floating to occur after insertion into this slot.

Next, the system adjusts the position of the pickup roller 6 in order that the adhesive sheet 2 fixed to the engaging groove 5a can be set perpendicular to the surface of the substrate 1. The bottom surface of the pickup roller 6 remains in contact with the upper surface of the adhesive sheet 2 set to the upper surface of the substrate 1, while the auxiliary roller 9 remains in contact with the surface of the substrate 1 so that the relative position between the surfaces of the pickup roller 6 and the substrate 1 can be held constant. In the next step, the adhesive sheet 2 is wound onto the pickup roller 6 in the state of exposing the adhesive-agent-coated layer outside as the pickup roller 6 rotates itself on the substrate 1 in the arrowed direction at a constant speed. FIG. 4 is the representation of the state of peeling off the adhesive sheet 2 from the substrate 1 by a specific length l1 from the position shown in FIG. 3. Since the length l1 peeling off the adhesive sheet 2 from the substrate 1 and the length l2 corresponding to the amount of the rotation of the pickup roller 6 over the surface of the substrate 1 is equal to each other, 90° can constantly be held independent of the flatness and curvature of the surface of the substrate 1.

Figure 5:
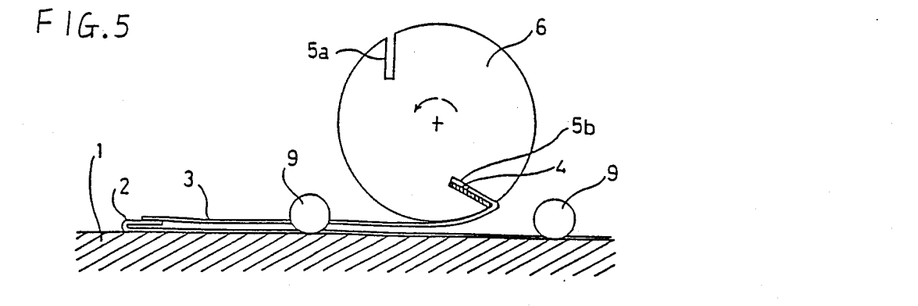
FIG. 5 is the schematic diagram illustrating the state when starting with the adhesive-strength measuring operation by implementing 180° -peeling with the apparatus shown in FIGS. 1 and 2.

Referring now to FIG. 5, the method of measuring the adhesive-strength based on the 180° -peeling mode related to the invention is described below. When this mode is underway, the header unit of either the adhesive sheet 2 of the lead-in tape 3 is inserted into the engaging groove 5b formed in the position symmetrically being opposite from the egaging groove 5a. FIG. 5 is the representation of the state when starting with the adhesive-strength measuring operation under the 180° -peeling mode. When this mode is entered, the peeled portion of the adhesive sheet 2 passes through the adhered portion of this sheet 2. Care should be taken when both portions of the adhesive sheet 2 are either in slight contact with each other or slightly apart from each other so that the friction force between both portions will not adversely affect the detected torque. To achieve this, compared to the 90° -peeling mode, the system causes the auxiliary roller 9 to project itself further below the base plate 18 by a length slightly longer than the thickness of the adhesive sheet 2 in order to securely generate gaps longer than the thickness of the adhesive sheet 2 between the surface of the adhesive sheet 2 set to the substrate 1 and the pickup roller 6.

The tip portion of the adhesive sheet 2 is folded back from the portion peeled off from the surface of the substrate 1. The folded-backed tip portion is then led through the gap, i.e., through the bottom surface of the pickup roller 6, amd then, it is held inside of the engaging groove 5b formed in the pickup roller 6.

When the 180° -peeling mode is underway, the adhesive-strength measuring apparatus itself is secured to a specific position of the substrate 1 in order that the apparatus itself will not shift its position. Accordingly, the adhesive sheet 2 is wound onto the pickup roller 6 in the state of keeping the adhesive-agent-coated layer inside by causing the pickup roller 6 to rotate itself in the arrowed direction exactly at the secured position. While the winding operation is underway, since the adhesive-agent-coated surface of the adhesive sheet 2 may adhere to the surface of the pickup roller 6, it is desirable that the surface of the pickup roller 6 be fully coated with silicon or poly-tetra-fluoroethylene resin (TEFLON).

Figure 6:
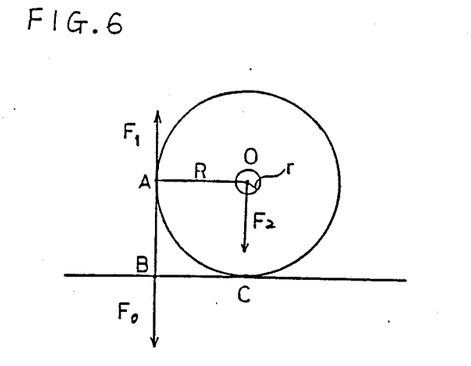
FIG. 6 is the chart illustrating the adhesive-strength, detected torque, and the force applied to bearing when measuring the adhesive-strength.

Referring now to FIG. 6, the relationship between the adhesive force Fo and the detected torque T when executing the method of measuring the adhesive-strength and the principle of generating the adhesive-strength according to the invention are described below.

FIG. 6 is the chart illustrating the relationship of the adhesive strength, detected torque, and the force applied to bearing when measuring the adhesive-strength. Adhesive-strength Fo, stripping force F1 resisting the adhesive-strength Fo, detected torque T, raduis R of the pickup roller, raduis r of bearing, bearing friction coefficient $\mu$, and the force applied to bearing respectively make up specific relationships shown below. The adhesive strength Fo applied to the pickup roller functions as the force F2 applied to the center 0 and the couple of forces RFo.

$$F2 = F1 = Fo \quad (1)$$
$$T = RFo + rF2$$
$$= Fo(R + \mu r)$$
$$= FoR(1 + \mu r/R) \quad (2)$$

When either a ball bearing or needle bearing is used, the bearing friction coefficient $\mu$ is represented to be $\mu = 0.001$ through 0.003. Since the radius R of the pickup roller is larger than the radius r of the bearing, according to the equation 2 shown above, the detected torque T becomes approximately Rfo. Since the adhesive strength Fo is proportional to the detected torque T, the adhesive-strength Fo can precisely be measured by detecting torque T.

Figure 7:
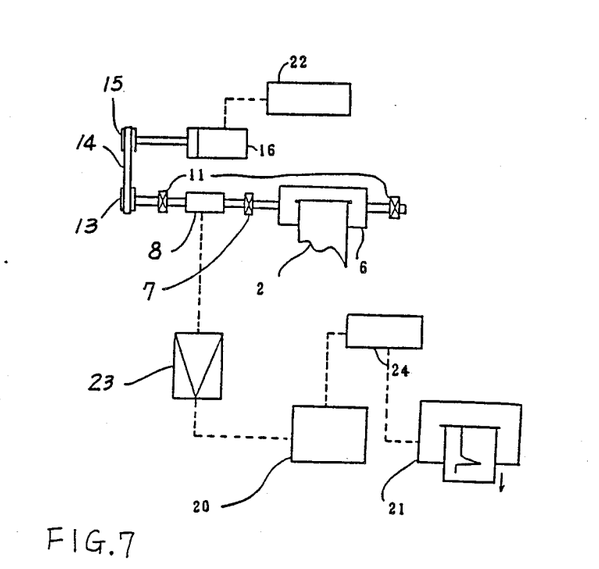
FIG. 7 is the simplified block diagram illustrating the constitution of one of the preferred embodiments of the adhesive-strength measuring apparatus according to the invention.

Referring now to FIG. 7, systematic operation of the adhesive-strength measuring appartus according to the invention is described below. FIG. 7 is the simplified block diagram of a preferred embodiment of the adhesive-strength measuring apparatus related to the invention. Pickup roller 6 is driven at a constant rotating speed by drive means. Speed controller 22 properly adjusts the speed of the rotation of the pickup roller, i.e., the speed of peeling the adhesive sheet 2 from the substrate. Mode select switch changes the direction of the rotation of the pickup roller 6.

While the rotating pickup roller 6 peels off the adhesive sheet 2 from the substrate 1, torque dectector 8 detects the torque applied to the pickup roller 6 in accordance with the principle mentioned above. The detected output signal is displayed as adhesive-strength by display means. For example, the adhesive-strength is first amplified by amplifier circuit block 23, which is then displayed in digital value by digital system 20 or in analog value by any analog display means. The output analog signal can also be recorded by recorder 21 simultaneous with the display. Display and recording of output analog value are properly controlled by controller 24. According to the adhesive-strength measuring apparatus and method according to the invention, adhesive-strength at the time of peeling off the adhesive sheet from the stripped sheet can also be measured. When this measurement is underway, since the peeling strength to be measured is negligible, measurement, display, and recording of the adhesive-strength are respectively executed by setting the display range low.

Figure 8:
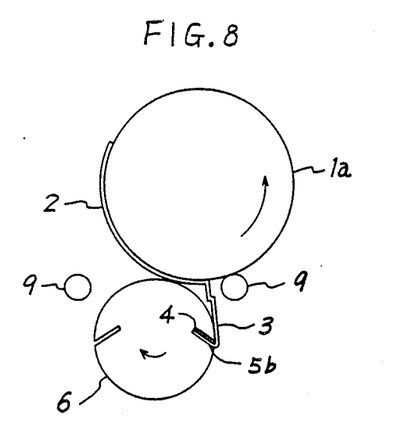
FIG. 8 is the schematic diagram illustrating the principle of measuring adhesive-strength of adhesive sheet set to the circumferential surface of a cylindrical substrate in accordance with the invention.

When measuring the adhesive-strength of the adhesive sheet adhered to the external surface of cylindrical subtrate 1a by applying the adhesive-strength measuring apparatus according to the invention, as shown in FIG. 8, the apparatus is first secured to an adequate frame (not shown) in order that the auxiliary roller 9 can face upward. Next, a pair of auxiliary rollers 9 and the pickup roller 6 firmly support the substrate 1a adhered with the adhesive sheet 2. Then, the tip end of the adhesive sheet 2 is adhered with the lead-in tape 3. After firmly securing the lead-in tape 3 to the engaging groove 5b via the head chip 4, the drive unit rotates the pickup roller 6 so that the measurement of the adhesive-strength can be executed.

Figure 9:
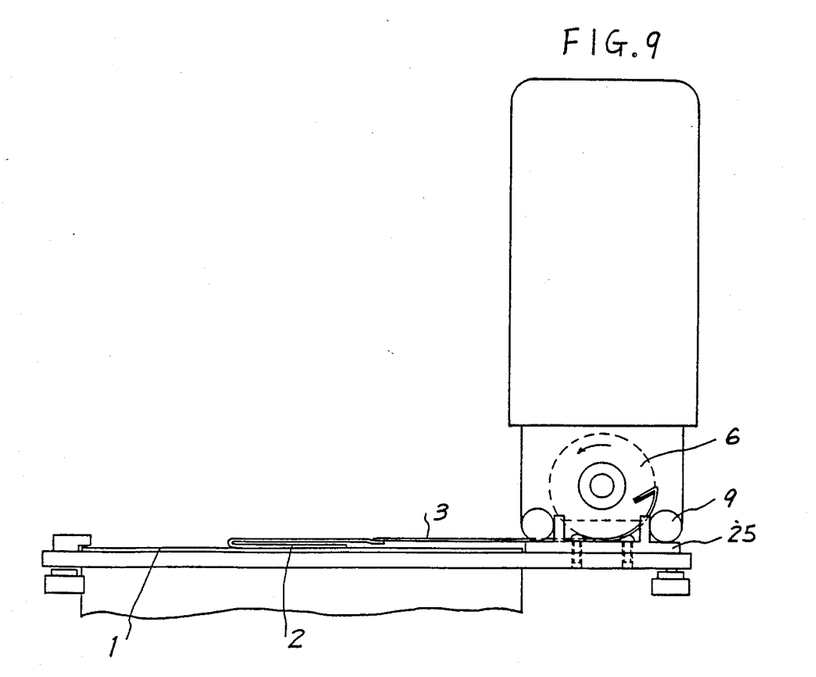
FIG. 9 is the simplified lateral view of the adhesive-strength measuring apparatus shown in FIGS. 1 and 2 using an additional gap-forming plate.

In particular, gap-formation plate 25 shown in FIG. 9 can effectively be used as means for easily changing the forward and backward movement of the auxiliary rollers instead of adjusting this movement when the 90°-peeling mode should be shifted to the 180°-stripping mode by applying the adhesive-strength measuring apparatus shown in FIGS. 1 through 6. In FIG. 9, the gap-formation plate 25 is provided with a specific thickness projecting itself by a specific height to allow the adhesive sheet 2 to return and slide its position from the surface of the substrate 1.

Substantially, the gap-formation plate 25 is of rectangular shape having four concaves and remains in contact with auxiliary roller 9 at its upper surface for constraining the rotation of these auxiliary rollers 9. Since the gap-formation plate 25 is set to the position adjoining the substrate 1 while relatively being secured to it, the apparatus can smoothly execute the adhesive-strength measuring operation under the 180°-peeling mode. More particularly, when the 180°-peeling mode is underway, since the substrate 1 and the apparatus are relatively secured to each other, the apparatus can smoothly wind the lead-in tape 3 onto the pickup roller 6, merely by rotating it, thus allowing the apparatus to properly execute the adhesive-strength measuring operation. After completing the adhesive-strength measuring operation under the 180°-peeling mode, the adhesive-strength measuring operation under the 90°-peeling mode can smoothly be executed by merely removing the gap-formation plate 25 from the apparatus.

Figure 10:
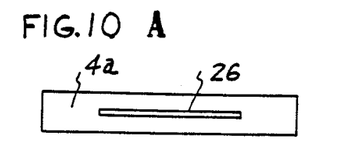
Figure 10C:
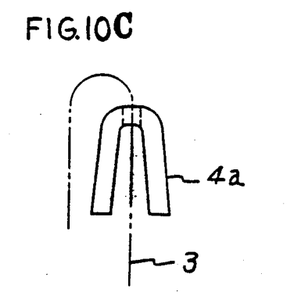
Figure 11:
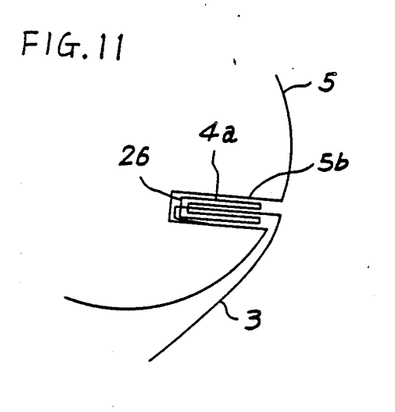
FIG. 11 is the simplified lateral view illustrating the state of fixing the tip end of a lead-in tape to the pickup roller using any of the head-chips shown in FIG. 10.

FIG. 10-A through C are illustrations of another embodiment of the head chip attached to the tip end of the lead-in tape 3. As shown in FIG. 10-A, the head chip 4a made from either plastic piece or any other sheet material piece is of rectangular shape having a greater dimension than the width of the tip end of the lead-in tape 3, while the head chip 4a is provided with slit 26 along the central-longitudinal line for allowing insertion of the tip end of the adhesive sheet 2. As shown in FIG. 10-B and C, both side portions of the slit 26 are close to each other and bent so that both sides face each other at a slightly open angle. The folded-back portion (including slit) of the head chip 4a has a width which is slightly less than the remaining part of the thickness of the lead-in tape 3 substracted from the width of the engaging groove 5b. FIG. 11 denotes the state in which the tip end of the lead-in tape 3 is inserted into slit 26 of the head chip 4a from the inner side of this head chip and then the tip end of the lead-in tape 3 projected from the slit 26 is folded back along either of the external surfaces of the head chip 4a before eventually being inserted into the engaging groove 5b of the pickup roller 6. When this state is present, since both sides of the head chip 4a normally face each other at an acute angle which is slightly wider than the parallel and are respectively provided with adequate elasticity, when both sides of the head chip 4a are inserted into the engaging groove 5b from the slit 26, since both sides of the head chip 4a tightly press against both lateral surfaces of the engaging groove 5b and are resistant against the force generated from the friction with the tip end of the lead-in tape 3, even if a certain tension is applied to the lead-in tape 3, during tests, both sides of the head chip 4a cannot easily be removed from the engaging groove 5b. As a result, the head chip 4a according to the invention securely holds the tip end of the lead-in tape 3 without using adhesive agent and effectively prevents the tip end of the lead-in tape 3 from being pelled off from the engaging groove 5b.

Figure 12:
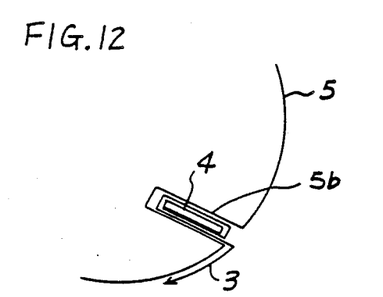
FIG. 12 is the simplified lateral view when applying a basic-shaped head-chip like FIG. 11.

When applying the rectangular-shaped head chip 4 mentioned above, as shown in FIG. 12, not only in the case of merely winding the tip end of the lead-in tape 3 in the direction of allowing the lead-in tape 3 to be inserted into the engaging slot from the position behind the rotating pickup roller 6 shown in FIG. 12 without using adhesive agent, but also when fixing the tip end of the lead-in tape 3 with adhesive agent, the position of the lead-in tape 3 engaged with the head chip is inverted by transferring the header unit from the engaging slot 5a to engaging slot 5b. When the lead-in tape 3 is engaged with head chip 4 in the state shown in FIG. 12, since there is no adverse effect from the pressing and inhibiting function in the pull-out direction between the lateral surfaces of the engaging slot 5b and the header unit as shown in FIG. 11, it is clearly understood that the header unit can easily be pulled outside of the engaging slot 5b if the adhesive strength of the tested adhesive sheet, in other words, if the tension during test, is too strong.

Industrial Applicability

The adhesive-strength measuring apparatus for implementing the method according to the unvention features compact constitution and portablilty, which is capable of quickly measuring adhesive strength of an adhesive sheet to the substrate at the location of using the adhesive sheet without shifting the position of the substrate itself. Furthermore, since it is possible for the apparatus according to the invention to correctly measure the adhesive-strength of the adhesive sheet adhered to any substrate having either the horizonal or vertical surface, or the curved surface, the measurement-applicable range can be extended. In addition, the adhesive-strength measuring apparatus according to the invention precisely measures the adhesive-strength by correctly maintaining the peeling speed and angle in either of the 90°-and-180°-peeling modes.

We claim:

1. A method of measuring an adhesive strength comprising the steps of:
   keeping the peripheral surface of a pickup roller at a level slightly heightened from the surface of a substrate adhered with an adhesive sheet such that the uppermost portion of the peripheral surface of said of pickup roller faces the top surface of said adhesive sheet on the substrate, by contacting an auxiliary roller projecting from a machine frame with the surface of a substrate;
   securing the tip end of either the adhesive sheet or a lead-in tape leading said adhesive sheet to engaging means of said pickup roller;
   setting a specific peeling angle for peeling said adhesive sheet from the surface of said substrate;
   pulling said adhesive sheet by rotating said pickup roller at a constant speed while maintaining the set angle;
   peeling off said adhesive sheet from said substrate, and subsequently winding it onto said pickup roller;
   detecting the torque of said pickup roller by means of a torque detector; and
   displaying and/or recording adhesive-strength of said adhesive sheet to said substrate based on signals output from said torque detector.

2. The method of measuring adhesive strength defined in claim 1, further comprising the steps of: first securing the tip end of either an adhesive sheet or lead-in tape leading said adhesive sheet to engaging means of said pickup roller; adjusting the position of said auxiliary roller projecting from said machine frame of the adhesive strength measuring apparatus while said auxiliary roller remains in contact with the surface of said substrate in order that either said adhesive sheet or said lead-in tape leading said adhesive sheet between said substrate and engaging means can be set perpendicular to the surface of said substrate and a sectional circumferential point on said pickup roller dealing with said adhesive sheet comes into contact with the back surface of said adhesive sheet adhered to the surface of said substrate, and wherein said adhesive sheet is then wound onto said roller with the adhesive agent-coated layer outwardly being exposed by causing said pickup roller to roll on said substrate with said adhesive sheet to displace the position of said roller on said substrate, thereby allowing the adhesive strength measuring apparatus to implement the measurement of the adhesive strength of said adhesive sheet when it is peeled by 90°, or the right angle from said substrate.

3. The method of measuring adhesive strength defined in claim 1, wherein a predetermined gap wider than the thickness of said adhesive sheet is securely provided between the back surface of said adhesive sheet adhered to said substrate and said pickup roller in the state in which said auxiliary roller remains in contact with the back surface of said substrate by means of adjusting the distance of said auxiliary roller projecting from said frame of the adhesive strength measuring apparatus, and then, the tip end of either said adhesive sheet or said lead-in tape is secured to engaging means provided for said pickup roller from the peeled-off position through the bottom surface of said pickup roller in order that the free tip portion and/or the peeled-off portion from said substrate adhered with said adhesive sheet can pass through said gap over the portion of said adhesive sheet adhered to said substrate, wherein said adhesive sheet is then wound onto said pickup roller with the adhesive agent-coated layer inwardly being disposed by causing said pickup roller to rotate at the present position above said substrate, thereby allowing the adhesive strength measuring apparatus to implement the measurement of the adhesive strength of said adhesive sheet when it is peeled from said substrate by 180° or by turning back along said substrate.

4. The method of measuring adhesive strength defined in claim 1, wherein a predetermined gap wider than the thickness of said adhesive sheet is securely provided between the back surface of said adhesive sheet adhered to said substrate and said pickup roller by applying a gap-formation plate for constraining the rotation of said auxiliary roller which is held for fixing the position relationship against said substrate while said auxiliary roller is in a position higher than the surface of said substrate, then, the tip end of either said adhesive sheet or said lead-in tape is secured to engaging means with it being turned up from the peeled-off position through the bottom surface of said pickup roller in order that the free tip portion and/or the portion of said adhesive sheet peeled-off from said substrate can pass through said gap over the portion of said adhesive sheet adhered to said substrate, and wherein said adhesive sheet is then wound onto said pickup roller with the adhesive agent-coated layer inwardly being disposed by causing said pickup roller to rotate at the present position above said substrate thereby allowing the adhesive strength measuring apparatus to implement measurement of the adhesive strength of said adhesive sheet when it is peeled from said substrate by 180°, or turning back along said substrate.

5. An adhesive-strength measuring apparatus comprising: a pickup roller which is provided with engaging means for engaging a free end of either an adhesive sheet with which the surface of a substrate is adhered, or a lead said adhesive sheet, said egaging means being substantially groove which makes up an acute angle against the tangent of the circumference of said pickup roller on the extended side from said adhesive sheet at the engaging point in order that either said adhesive sheet or lead-in tpae can securely be engaged by means of inserting a head chip secured to tip end of said adhesive sheet or lead-in tape into said groove;
   a plurality of auxiliary rollers for contacting the surface of the substrate adhered with said adhesive sheet to keep the peripheral surface of said pickup roller at a level slightly heightened from the surface of said substrate such that the undermost portion of the peripheral surface of said pickup roller faces the top surface of said adhesive sheet on the substrate;
   drive means for said pickup rotating roller at a constant speed;
   torque detection means for generating output signals by detecting the torque of said pickup roller; and
   display means for displaying adhesive strength of said adhesive sheet to said substrate based on the output

* * * * *